United States Patent [19]
Evans et al.

[11] Patent Number: 5,267,573
[45] Date of Patent: Dec. 7, 1993

[54] GUIDEWIRE EXTENDER

[75] Inventors: Scott M. Evans, Tustin; Vince Divino, Mission Viejo, both of Calif.

[73] Assignee: Oakley, Inc., Irvine, Calif.

[21] Appl. No.: 975,843

[22] Filed: Nov. 13, 1992

[51] Int. Cl.⁵ .............................. A61B 5/00
[52] U.S. Cl. ............................ 128/772; 604/95
[58] Field of Search ............. 128/657, 772; 604/95, 604/164, 166, 170, 171, 283; 403/229, 296

[56] References Cited

U.S. PATENT DOCUMENTS

| | | | |
|---|---|---|---|
| 4,827,941 | 5/1989 | Taylor et al. | 128/772 |
| 4,875,489 | 10/1989 | Messner et al. | 128/657 |
| 4,917,103 | 4/1990 | Gambale et al. | 128/772 |
| 4,922,923 | 5/1990 | Gambale et al. | 128/772 |
| 4,966,163 | 10/1990 | Kraus et al. | 128/772 |
| 5,031,636 | 7/1991 | Gambale et al. | 128/772 |
| 5,109,867 | 5/1992 | Twyford, Jr. | 128/772 |
| 5,117,838 | 6/1992 | Palmer et al. | 128/772 |
| 5,133,364 | 7/1992 | Palermo et al. | 128/772 |
| 5,147,317 | 9/1992 | Shank et al. | 128/657 |

*Primary Examiner*—Max Hindenburg
*Attorney, Agent, or Firm*—Knobbe, Martens, Olson & Bear

[57] ABSTRACT

A guidewire extender particularly suited for use in percutaneous transluminal coronary angioplasty. A tubular connector member attaches to the proximal end of a steerable guidewire. A helical coil bonded to a male insertion segment of a proximal extension member contacts an inward depression on the tubular connector. The extension member mates with the tubular connector to extend the guidewire by rotating the extension member to advance the helical coil past the depression. Some axial play between the coupled components is possible. The extension member locks to the guidewire without special tools. Manufacture and assembly are simplified.

13 Claims, 3 Drawing Sheets

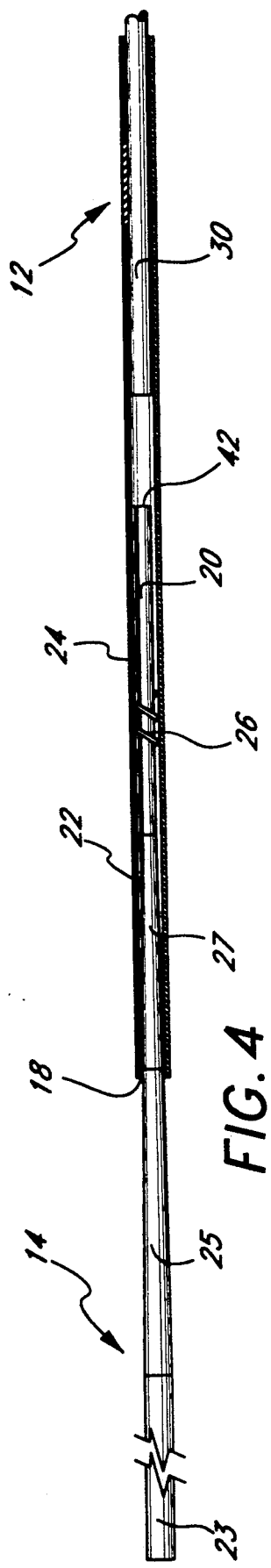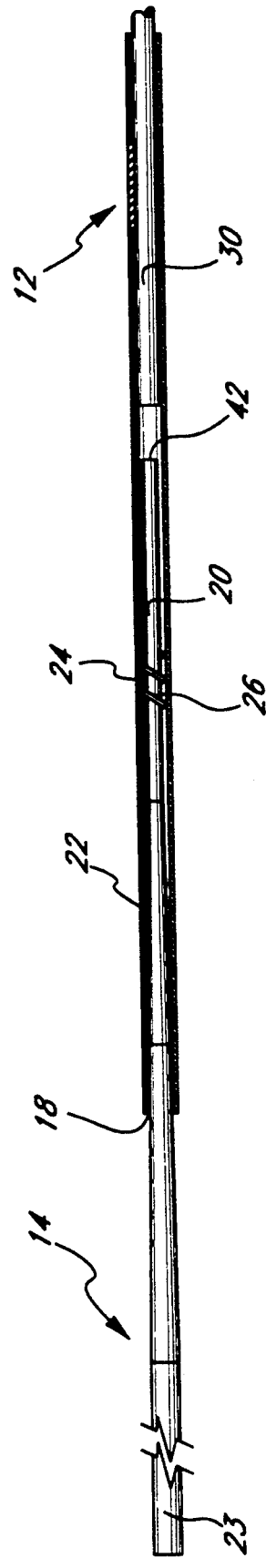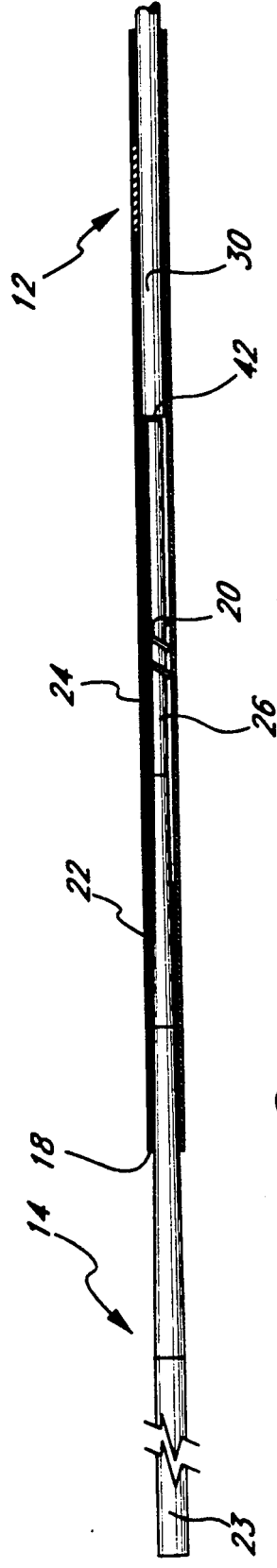

GUIDEWIRE EXTENDER

BACKGROUND OF THE INVENTION

The present invention relates generally to guidewires for catheters and the like, and more particularly to a guidewire for use in a percutaneous transluminal coronary angioplasty procedure.

Medical catheters generally comprise elongate tube-like members which may be inserted into the body, either percutaneously or via a body orifice, for any of a wide variety of diagnostic or therapeutic purposes. Such medical applications frequently require use of a guidewire to facilitate the placement of catheters in the arterial system and other body lumen of a patient, particularly with regard to certain cardiovascular applications.

One such application requires manipulation of a guidewire from a position outside the patient's body through extended portions of the patient's arterial system to a position proximate a stenotic site. Stenosis is an abnormal narrowing of a passage or canal in the body, commonly associated with atherosclerosis, or blocking of the arteries with plaque. A balloon dilatation catheter is then mounted over the guidewire and advanced to the treatment site. The procedure expands intravascular lesions of soft or hard thrombotic or atheromatous material and is more formally known as Percutaneous Transluminal Coronary Angioplasty (PTCA). In a typical PTCA procedure, the guidewire is percutaneously inserted into the brachial or the femoral artery, and transluminally advanced to the stenotic region of the coronary artery.

Once a guidewire has been placed across a stenosis in the artery, the balloon catheter or other treatment or diagnostic catheter is advanced along or over the guidewire to the treatment site. On occasion, the treatment or diagnostic catheter is advantageously removed and replaced by a different catheter during the course of the procedure. In order to ensure that the guidewire is not dislodged from its position in the artery during removal of the catheter, the proximal portion of the guidewire extending out of the patient must be sufficiently longer than the overall length of the treatment catheter so that it can be firmly grasped throughout the removal of the treatment catheter. Conventional guidewires for use in PTCA applications are not long enough for this purpose.

Guidewires currently used for percutaneous transluminal coronary balloon angioplasty applications generally range in length from 100 to 200 cm with a typical dilatation catheter on the order of 130 to 145 cm long. Given the distance the guidewire must be inserted into the patient, the proximally projecting portion may be less than the length of the catheter.

Current guidewire extensions typically include some means for coupling an extension to a main guidewire to provide an added length over which to retract the catheter. One such device is shown in U.S. Pat. No. 4,966,163 to Kraus, et al. The device utilizes a combined extension and coupling member to ensure axial alignment with a main guidewire section yet allow rotational movement therebetween. The device disadvantageously requires a substantial amount of machining of the three independent mating parts.

Thus, there remains a need for a guidewire which is especially suited for procedures such as percutaneous transluminal coronary angioplasty possibly requiring a catheter replacement. In particular, the guidewire should be simply constructed and utilized such that catheters may be replaced without dislodging the guidewire.

SUMMARY OF THE INVENTION

In accordance with the preferred embodiment, the present invention provides a guidewire system which may be extended to facilitate replacement of operating catheters. An extension section advantageously couples to a main guidewire section while allowing free axial rotation therebetween. The extension section readily couples and securely locks to the distal section without special tools to prevent axial separation during the catheter replacement procedure. The coupling means provides a quick and easy detachment. Advantageously, the manufacture of the components requires a minimum of machining of the actual guidewire and extension sections and instead makes use of a simple coupling tube designed to bond to one of the sections and releasably receive the other section on which a coil member has been bonded.

The present invention provides a guidewire system with a proximal extension section adapted to couple with a projecting end of a guidewire section allowing a catheter to be retracted and replaced without losing a grip on at least one portion of the guidewire system. The coupling joint includes a helical coil bonded to the distal end of one of the sections. The outer diameter of the bonded coil fits within a tube secured to the end of the opposing section. The section including the helical coil may be rotated to advance the coil past an inner protrusion of the tube and join the extension and guidewire sections. The clearance within said tube at the protrusion is greater than the diameter of the distal end of the section to which said coil is fixed, yet less than the outer diameter of said helical coil.

Thus, there is provided in accordance with one aspect of the present invention a guidewire extender for permitting the effective extension of the proximal portion of the guidewire to allow removal of a treatment catheter while leaving the guidewire in place. A proximal extension member includes a constant diameter portion tapering down one or more times to a reduced diameter male connector portion. A helical coil, with the adjacent loops spread apart axially, bonds to the exterior of the male connector portion. The male connector portion and helical coil insert within a tubular coupling attached to the proximal end of a guidewire. Subsequent to rotating the helical coil past an inwardly extending dimple on the tubular coupling, the distal end of the male connector portion is blocked by the proximal end of the guidewire core. The extension section thus effectively lengthens the guidewire and is coupled thereto with some axial play.

These and further features and advantages of the present invention will become apparent from the detailed description of preferred embodiments which follows when considered together with the attached drawings and claims.

BRIEF DESCRIPTION OF THE DRAWINGS

FIG. 1a is a detail view of a dimple in a tubular coupling section of the guidewire extension system as seen along lines 1a-1a of FIG. 1.

FIG. 4 is a partial cut-away view showing the proximal extension section partially inserted into the tubular coupling section with the helical coil proximal to the dimple.

FIG. 5 is a partial cut-away view as in FIG. 4 with the helical coil straddling the dimple.

FIG. 6 is a partial cut-away view as in FIG. 4 showing the extension section fully inserted into the tubular coupling with the helical coil distal to the dimple.

DETAILED DESCRIPTION OF THE INVENTION

Figure 1:
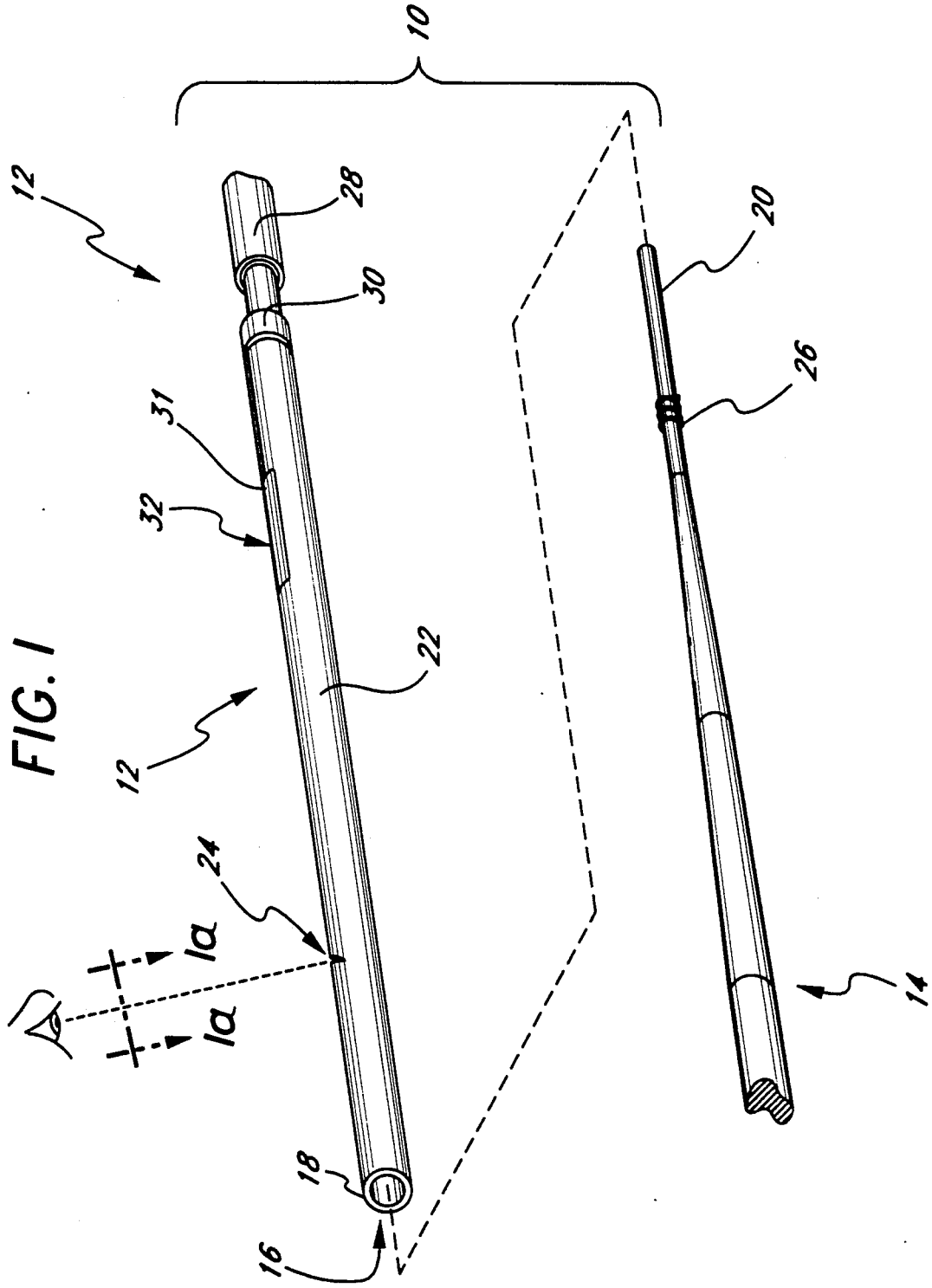
FIG. 1 is a perspective view of the guidewire extension system of the present invention.

Referring to FIG. 1, there is disclosed an extendable guidewire system 10. Guidewire system 10 comprises a distal portion 12, for insertion into the patient, and a proximal extension section 14 for releasably engaging the distal portion 12 to effectively lengthen the overall guidewire system 10.

The percutaneous transluminal coronary angioplasty procedure for outwardly compressing a plaque deposit within an artery is generally accomplished as follows: an introducer sheath and a gliding catheter (not shown) are inserted into a small incision in the femoral or brachial artery, and the balloon catheter is advanced to the ostium. A guidewire is typically preloaded within a balloon catheter so that the entire assembly can be advanced through the introducer sheath and past the ostium to the stenotic region. The distal tip of the guidewire is adapted for steering through the coronary or other branch arteries to the stenosis. In certain applications, only the guidewire may be inserted with a catheter advanced over the wire later. The surgeon manipulates the guidewire through often tortuous, convoluted arterial passageways within the heart by torquing or otherwise steering the guidewire. A radiopaque marker or other indicator is used to assist the surgeon in locating the distal tip of the guidewire and positioning it at the stenotic region. After the assembly is in position, the balloon dilatation catheter (not shown) is advanced distally until the balloon is positioned near the treatment site and a short length of guidewire extends proximally from the catheter outside of the patient's body. While the present embodiment is described in conjunction with a coronary application, the extension system 10 may be applied to other non-coronary procedures.

Distal portion 12 comprises a tubular aperture 16 at its proximal end 18 for receiving a male connector section 20 which extends distally from proximal portion 14. Although the present invention will be described in terms of a male portion 20 on proximal portion 14 mating with a female recess 16 on distal portion 12, the relationship of the female and male components of the present invention can be readily reversed as will be apparent to one of skill in the art.

In accordance with one preferred embodiment of the present invention, distal portion 12 comprises at its proximal end a tube or sleeve 22 having an outside diameter of approximately 0.014 inches and an inside diameter of approximately 0.01 inches. Particular dimensions of embodiments of the present invention can be readily varied to suit specific applications as will be apparent to one of skill in the art. The tubular sleeve 22 is provided with at least one radially inwardly extending protrusion or dimple 24, reducing the interior cross-sectional area of the lumen extending through tubular sleeve 22 at that point.

Referring to the detail of FIG. 1a, the dimple 24 comprises an inward indentation in the wall of the sleeve 22 forming a line at an angle with the axis. Alternatively, the dimple 24 may be a point indentation or other shapes, or a plurality of dimples may be provided in the sleeve 22. Such alternative arrangements must only be consistent with the capability of the illustrated line dimple 24 in cooperating with an outwardly projecting member or helical coil 26 on the proximal extension section 14, as will be described more fully below. The dimple 24 is preferably formed at a distance of approximately 0.15 inches from the proximal end of the sleeve 22 and, in a preferred embodiment, the dimple has a depth of approximately 0.002 inchdes and a maximum axial gap at the surface of about 0.0075 inches. In other words, a line spanning the outer edges of the dimple 24, and perpendicular to the angled centerline, reaches a maximum gap at the middle of approximately 0.0075 inches. The centerline of the dimple 24 forms an angle with the axis approximately equal to the angle formed by the helical coil 26 along the same axis when the extension system is assembled. Advantageously, the dimple 24 is formed with a single stroke of a forming tool applied on the exterior of the sleeve 22.

Figure 2:
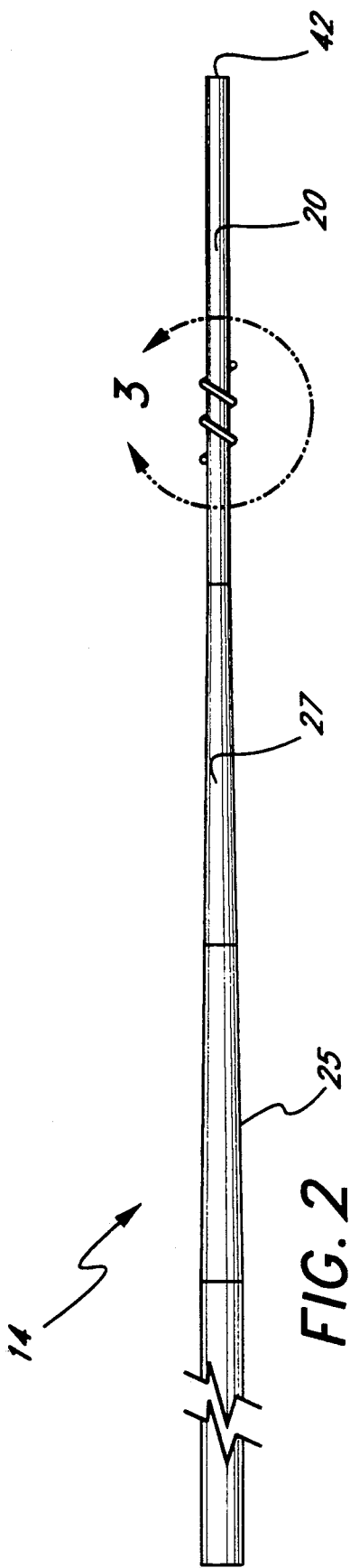
FIG. 2 is a side elevational view of a proximal extension section of the guidewire extension system.

As seen in FIG. 2, the proximal extension section 14 comprises an elongated wire having a nominal major diameter portion 23 and the aforementioned reduced diameter male portion 20 separated by one or more tapered regions. In the embodiment shown, two differently angled tapers 25, 27 transition the diameter of the extension 14 from the nominal section 23 to the reduced portion 20. The distal portion of the extension 14 terminates in a flat end 42.

The exterior surfaces of both the guidewire and the nominal diameter section 23 of the extension section are preferably smooth throughout, and optionally provided with an elastic, biocompatible coating or sheath to enhance the smooth outer surfaces. Suitable coatings can be formed by dipping, spraying, or wrapping, and heat curing operations, as are known in the art. A coating material should be selected which will permit sufficient flexing of the wire without cracking, will minimize sliding friction during insertion and removal of the coaxial catheter, and is substantially chemically inert in the in vivo vascular environment. A variety of suitable materials are known, including, for example, polytetrafluoroethylene (Teflon), urethane, polyethylene and silicon.

Figure 3:
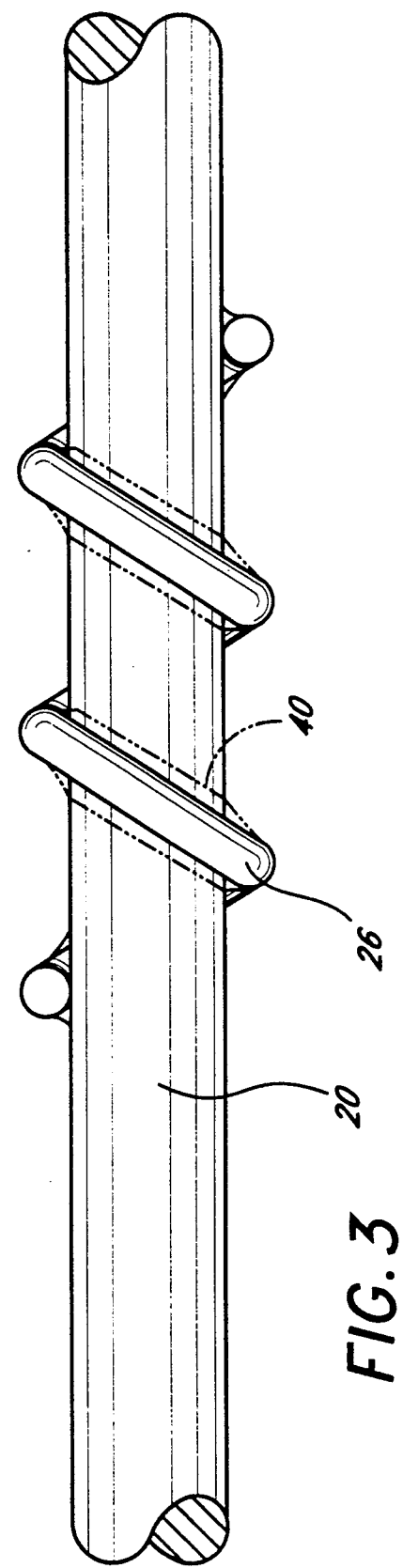
FIG. 3 is an enlarged side view of a helical coil shown in the region 3 of FIG. 2.

Referring to FIGS. 1-3, the helical coil 26 mounts to the distal portion 20 of proximal extension segment 14. The coil 26 is preferably formed by wrapping a wire either directly around male section 20, or around a mandrel and later mounted on the male section. In an embodiment in which the helical coil 26 is formed on a separate mandrel, the coil is axially prestretched prior to mounting on section 20 so that the adjacent loops are within the range of from about 0.0135 to about 0.0145 inches in the preferred embodiment. The helical coil is thereafter mounted on the section 20, and secured thereto such as by soldering, brazing or other techniques known in the art. As shown in FIG. 3, a helical bead of solder 40 extends the length of the coil 26. One type of preferred solder comprises 95% tin and 5% silver.

The helical coil 26 can be formed from stainless steel or blank wire having a circular cross-sectional configuration with a diameter within the range of from about 0.001 to about 0.003 inches. Alternatively, helical coil 26 can be formed from wire having a rectangular cross-sectional configuration, having cross-sectional dimensions within the range of from about 0.001 to 0.003 inches by from about 0.001 to 0.004 inches, or other variations known in the art.

In a preferred embodiment of the present invention, the guidewire extender system 10 is particularly adapted for use with a steerable guidewire such as that disclosed and claimed in issued U.S. Pat. Nos. 4,921,482 (5/1/90), 4,998,916 (3/12/91), 5,037,391 (8/6/91), and 5,108,368 (4/28/92), and also copending Patent Application Ser. No. 07/865,357, filed 4/8/92, the disclosures of which are hereby incorporated by reference. All of the referenced patents and application are owned by the present entity and disclose Steerable Angioplasty Devices.

As seen in FIG. 1, the main guidewire section of the present invention comprises a core wire 30 surrounded by a biocompatible sheath 29 extending to a distal steerable tip (not shown). The proximal end of the steerable guidewire section includes a short length of hypotube 28 as is well known in the art, bonded to the exterior of the core wire 30 on both ends with solder or braze material. The gap formed between the proximal end of the hypotube 28 and tubular coupling sleeve 22 need not be precise, however, the positioning of the core wire 30 within the tubular coupling sleeve directly affects the amount of axial play of the assembled extension system 10, as will be explained below. In the preferred embodiment, the outer diameter of the guidewire, comprising the outer diameter of the sheath 29, is preferably 0.014 inches, matching the OD of the tubular sleeve 22 and extension wire 14. The present guidewire extension system 10, however, may be utilized with a range of guidewire sizes preferably from 0.014 to 0.035 inches in diameter.

A sheath 29 extends from a position close to the hypotube 28 to the distal steerable tip (not shown) of the guidewire. The core wire 30 slides axially within the sheath 29. A hand manipulator (not illustrated) is provided with a means to grasp the hypotube 28 and the core wire 30, and controllably axially displace the core wire with respect to the outer sheath 29 of the guidewire to deflect the distal tip.

The proximal end of core wire 30 extends into the tubular sleeve 22, and is secured thereto by any of a variety of means well known in the art. As illustrated in FIG. 1, sleeve 22 includes an aperture 31 to conveniently permit the application of solder or braze material 32 directly to the core wire 30. The shape of the aperture 31 may be round or, as shown, rectangular, or any other configuration having a size permitting a sufficient bead of solder 32 to flow in order to ensure a good bond. Preferably, the corners of the aperture 31 are rounded with an approximately 0.002 inch radius to facilitate machining. The amount and application of solder 32 is such that the outer surface conforms closely with the tubular segment sleeve 22 to form a continuous surface for sliding a catheter thereover.

In one embodiment, the total length of the distal segment 12, including the guidewire and tubular sleeve 22, extends approximately 178 cm and the tubular section has a length of approximately 2 cm. Preferably, the solder aperture 32 has an axial length of about 0.5 inches, a depth of 0.004 to 0.005 inches, and the distal limit of the aperture is spaced approximately 0.15 inches from the distal end of tubular sleeve 22. The core wire 30, in one embodiment, has an outside diameter of 0.0095 inches and the inside diameter of the tubular sleeve 22 is 0.01 inches.

The components of the guidewire extender system 10 are preferably constructed of 304 Stainless Steel for strength and corrosion resistance. Other material having similar properties may be substituted however. The matching of materials for the tubular sleeve 22 and core wire 30 permits a more secure joinder therebetween by using a solder or braze which is particularly compatible to both components. Likewise, the soldered or brazed connection between the male portion 20 and helical coil 26 is enhanced by matching the construction materials. While the matching of the materials is preferred, suitable solder or braze alloy materials are well known to enable secure bonding of dissimilar metals. Alternatively, the proximal portion 14 may be constructed of a non-metallic material, such as nylon or a polymer, as long as the strength and rigidity of the proximal portion and helical coil 26 are sufficient to connect to the distal portion 12 and support a catheter slid thereover.

The guidewire extender system 10 couples together to provide an extended guidewire as follows, and as shown in FIGS. 4-6. The proximal extension segment 14 is inserted into the opening 16 on the proximal end of tubular sleeve 22. The proximal segment 14 is advanced distally until the helical coil 26 comes into contact with the proximal surface of the radially inwardly extending dimple 24. At that point, the proximal segment 14 is rotated such as between the thumb and forefinger of the clinician, to spin the helical coil 26 and permit distal advancement of the proximal section. Thus, the dimple 24 extends in the space between adjacent loops of the coil 26 to allow passage of the male portion 20 into the sleeve 22. At a minimum, the male portion 20 receives at least one complete loop of helical coil 26 to ensure an axial lock when the extension section 14 is coupled to the guidewire section. More preferably, the helical coil 26 includes at least two complete turns to more securely lock the components together, the adjacent loops being spaced between 0.0135 and 0.0145 inches apart. The coil 26 and dimple 24 preferably make a fifty degree angle with the longitudinal axis of the extension system 10.

The proximal limit of the helical coil 26 is spaced with respect to the distal end 42 of the male section 20 such that the entirety of the helical coil can be advanced distally of dimple 24. A proximal loop of the helical coil 26 thus contacts the dimple 24 to retain the extension 14 within the tubular sleeve 22. Due to the advancement of the coil 26 past the dimple 24, the extension 14 may freely spin within the sleeve 22. The distal end 42 contacts the proximal end of core wire 30 to obstruct farther advancement of the proximal segment 14 into the distal segment 12. Alternatively, contact between either of the tapers 25, 27 and the proximal end 18 of the sleeve 22 may obstruct farther advancement. In this manner, once it is installed in the tubular sleeve 22, the extension segment 14 is constrained axially but can freely rotate with respect to the distal segment 12, and therefore, the extension cannot cause twisting of the distal guidewire. The extension section 14 may rotate completely around in a 360 degree arc any number of times without affecting the distal segment 12, which is particularly useful when the distal segment and guidewire have been bent to conform to a patient's anatomy. Any twisting imparted to the distal portion 12 may result in trauma to the internal tissue of the patient.

In the illustrated embodiment, a slight axial play exists in the assembled guidewire extender system 10. As stated above, the proximal segment 14 is obstructed from further advancement into the tubular sleeve 22 by one of two ways. The retraction, conversely, is restricted by the helical coil 26 contacting the distal side of the dimple 24. Some axial space exists between these two impediments to movement such that the extension section 14 may slide axially a short distance. This axial play may be in the range of 0.003 to 0.03 inches. The fixed position of the core wire 30 within the tubular sleeve 22 in combination with the dimple 24 placement and helical coil 26 location along the male section 20 determine the amount of axial play. The tolerances associated with the various axial dimensions along the length of the guidewire extender system have a minimum total range of 0.001 inches, and in most instances can range a total of 0.01 inches. The axial play, therefor may vary as a result and compensate for such tolerances. Alternatively, the distal and proximal segments 12, 14 may couple together without any axial play whatsoever and still satisfy the inventive concepts described herein.

In alternate embodiment of the present invention, a male section on a proximal extension member can be provided with a radially outwardly extending projection, for engaging a helical coil positioned on a radially interior surface of a corresponding female section. Furthermore, it is possible that a tubular sleeve attaches to the extension section and the male portion including a helical coil is formed on the proximal end of the guidewire core wire, in a reversed situation from the illustrated embodiment. Such alternative arrangements are quite within the scope of the invention, the inclusion of a single coil cooperating with a dimple to loosely axially hold yet rotationally decouple the extender and guidewire being sufficient to meet the present invention's unique and advantageous attributes.

Suitable extension wire 14 may be prepared in any of a variety of manners which can be readily devised by one of skill in the art. In one embodiment, a spring hardness solid stainless steel wire of 0.014 inch diameter and 150 cm length is obtained from sources known to those skilled in the art. The wire is thereafter preferably straightened to industry standards or, in other words, to a straightened condition suitable for subsequent centerless core grinding.

The straightened wire is thereafter ground to the desired profile using conventional techniques. The grinding operation must produce surfaces having tolerances of $+-0.0002$ inches. Preferably, the reduced portion 20 is ground to a diameter of between 0.0052 and 0.0055 inches, so that when wrapped with 0.002 inch thick helical coil wire 26, the assembled diameter through the coil will be slightly less than 0.010 inches.

The coil 26 is thereafter wound or mounted around the reduced male connector region 20. The coil 26 may be constructed in any of a variety of ways known in the art, such as by tightly winding a coil of wire directly around the male connector 20, or by separately winding the coil and mounting the coil onto the connector as a separate step. In the latter method, the coil 26 is preferably wound around a rotating mandrel having a diameter equal to or slightly smaller than the diameter of the reduced connector region 20, to ensure a snug fit in the assembled wire.

Preferably, 0.002 inch diameter wire stack is wound into a coil over a 0.0046 inch diameter mandrel. The coil 26 springs open slightly upon release from the mandrel to approximately a 0.005 inch inside diameter. The coil 26 is thereafter slid onto the connector portion 20, and soldered along its length.

The simple procedures for fabricating and assembling the guidewire extension system 10 make the present invention highly desirable over extension systems of the prior art. Advantageously, the machining for the coupling surfaces is done with conventional processes and is easily achievable without special expense. There are no threads to cut and no unusually tight tolerances to meet. Especially beneficial is the no machining is required on the long guidewire section at all and only a minimum amount of machining is necessary on the extension section. A majority of machining is done on the tubular sleeve 22 which is relatively easy to handle. In assembly, the helical coil 26 simply slides over to bond to the male portion 20. The acceptability of axial play in the assembled system 10 erases the need to highly accurately position the coil 26 along the male portion 20. The exposed coil 26 advantageously presents an easily accessible surface on which to apply a bonding agent. The window 31 in the tubular sleeve 22 is readily formed to provide a handy means for joining the sleeve to the core wire 30. Moreover, the dimple 24 on the sleeve 22 is formed with a single stroke of a forming tool. Finally, the elegance of having only two elements, a distal 12 and a proximal 14, which couple together to extend the guidewire provides a time-saving benefit during an operation.

Although this invention is described in terms of certain preferred embodiments, other embodiments that will be apparent to those of ordinary skill in the art are also within the scope of this invention. Accordingly, the scope of the invention is intended to be defined by the claims that follow.

We claim:
1. A guidewire system, comprising:
   an extension section;
   a main guidewire section, one of which sections having a working portion, wherein a helical coil is secured to the outside of one of said sections, and a tube sized to receive said portion of said one of said sections upon which said helical coil is fixed is secured to another of said sections; and
   at least one inward protrusion on the interior of said tube which reduces the clearance within said tube to a distance greater than the diameter of said portion of said one of said sections to which said coil is fixed, yet less than the outer diameter of said helical coil, whereby said one of said sections may be rotated to advance said helical coil past said protrusion to lock said one of said sections to said other of said sections, yet permit said sections to freely axially rotate relative one another.
2. A guidewire system as in claim 1, wherein said one of said sections is said extension section and said another of said sections is said main guidewire section.
3. A guidewire system as in claim 2, wherein said helical coil is soldered to said extension section.
4. A guidewire system as in claim 2, wherein said helical coil is brazed to said extension section.
5. A guidewire system as in claim 2, wherein said helical coil is welded to said extension section.
6. A guidewire system as in claim 1, wherein said one of said sections is constrained from farther advancement once said helical coil has traveled past said protrusion by said sections abutting one another which said tube.

7. A guidewire system as in claim 1, wherein said one of said sections is constrained from farther advancement once said helical coil has traveled past said protrusion by an outwardly tapered portion of said one of said sections abutting said tube.

8. A guidewire system as in claims 6 or 7, wherein said extension section may move a slight axial distance relative to said tube once said helical coil has traveled past said protrusion.

9. A guidewire system as in claim 8, wherein said axial distance is between 0.003 and 0.03 inches.

10. A guidewire system as in claim 1, wherein said tube further comprises an aperture located near a distal end for application of bonding material to rigidly join said tube to said another of said sections.

11. A guidewire system, comprising:
an extension section, including a portion to which a member is secured;
a main guidewire section;
a tube sized to receive said portion of said extension section to which said member is secured and said main guidewire section; and
at least one inward protrusion on the interior of said tube which reduces the clearance within aid tube to a distance greater than the diameter of said portion of said extension section to which said member is fixed, yet less than the outer diameter of said member, whereby said extension section may be rotated to advance said member past said protrusion to lock said extension section to said guidewire section, yet permit said sections to freely axially rotate relative one another.

12. A guidewire system as in claim 11, wherein said extension section may move a slight axial distance relative to said guidewire section once said member has traveled past said protrusion.

13. A guidewire system as in claim 12, wherein said axial distance is between 0.003 and 0.03 inches.

* * * * *

UNITED STATES PATENT AND TRADEMARK OFFICE
CERTIFICATE OF CORRECTION

PATENT NO. : 5,267,573

DATED : 12/7/93

INVENTOR(S) : Evans et al.

It is certified that error appears in the above-indentified patent and that said Letters Patent is hereby corrected as shown below:

On the title page, item [73] Assignee: "Oakley Inc., Irvine, Calif." should read --Pilot Cardiovascular Systems, Inc., San Clemente, Calif.--.

Signed and Sealed this

Twenty-sixth Day of April, 1994

Attest:

BRUCE LEHMAN

*Attesting Officer*    *Commissioner of Patents and Trademarks*